United States Patent [19]
Ishida et al.

[11] Patent Number: 5,264,131
[45] Date of Patent: Nov. 23, 1993

[54] OXYGEN-DISSOLVING PROCESS AND AN APPARATUS FOR PRACTICING THE PROCESS

[75] Inventors: Masahiko Ishida; Harumi Matsuzaki, both of Hitachi; Ryusei Nakano, Kudamatsu, all of Japan

[73] Assignee: Hitachi, Ltd., Tokyo, Japan

[21] Appl. No.: 755,457

[22] Filed: Sep. 5, 1991

[30] Foreign Application Priority Data

Sep. 12, 1990 [JP] Japan ................................ 2-240138

[51] Int. Cl.$^5$ .............................................. B01D 61/38
[52] U.S. Cl. ........................................ 210/643; 95/54
[58] Field of Search .................... 210/490, 643; 55/16, 55/158; 204/157.6

[56] References Cited

U.S. PATENT DOCUMENTS

| | | |
|---|---|---|
| 3,958,014 | 5/1976 | Watanabe et al. |
| 4,734,112 | 3/1988 | Okita et al. .................... 210/490 |
| 4,761,164 | 8/1988 | Pez et al. ........................ 55/16 |
| 4,853,097 | 8/1989 | Marchionni et al. .......... 204/157.6 |

FOREIGN PATENT DOCUMENTS

| | | |
|---|---|---|
| 61-18402 | 7/1984 | Japan . |
| 61-35782 | 7/1984 | Japan . |
| 64-60368 | 3/1988 | Japan . |
| 2-767733 | 9/1988 | Japan . |
| 1-168274 | 11/1988 | Japan . |

OTHER PUBLICATIONS

Develop. biol. Standard., "Optimization of a Membrane Oxygenation System for a Cell Culture in Stirred Tank Reactors", vol. 66, pp. 263-268.

Develop. biol. Standard., "Bubble Free Cell Culture Aeration with Porous Moving Membranes", vol. 66, pp. 227-240.

*Primary Examiner*—Frank Sever
*Attorney, Agent, or Firm*—Antonelli, Terry, Stout & Kraus

[57] ABSTRACT

The present invention provides a process for dissolving oxygen comprising forming a liquid membrane of an oxygen-permeable liquid on a support layer made of a hydrophobic porous material, bringing one side of the liquid membrane into contact with an oxygen-containing gas and the other side with an aqueous liquor, and thereby dissolving oxygen in the aqueous liquor; a process for culturing cells in an oxygen-containing aqueous liquor obtained by the oxygen-dissolving process; and apparatus for practicing these processes. According to the present invention, oxygen can be dissolved in an aqueous liquor efficiently and economically, and aerobic cell-culturing can be stably effected even at a high cell concentration.

11 Claims, 4 Drawing Sheets

OXYGEN-DISSOLVING PROCESS AND AN APPARATUS FOR PRACTICING THE PROCESS

BACKGROUND OF THE INVENTION

The present invention relates to a process for dissolving oxygen in an aqueous liquor, a process for culturing cells in an oxygen-containing aqueous liquor obtained by the oxygen-dissolving process, and apparatus for practicing these processes.

In the present specification, the word "cells" includes animal cells, plant cells and microorganism cells unless otherwise specified.

The cultivation of cells, in particular, animal cells, is an important technique for producing useful materials such as drugs. In the aerobic cultivation of animal cells or microorganism cells, it is often necessary to supply oxygen dissolved in an aqueous liquor in an amount sufficient to meet the demand for oxygen the consumption of which increases with an increase of the cell concentration.

As methods for supplying oxygen, there have been known the following methods.

1) A method of blowing oxygen directly through a liquor.

2) A method of blowing an oxygen-containing gas against the free surface of a culture liquor and thereby diffusing oxygen from the surface of the liquor to the inside to dissolve oxygen in the liquor.

3) A method of placing an oxygen-permeable solid membrane so as to bring one side into contact with an oxygen-containing gas and the other side with a liquor, and thereby allowing oxygen to permeate the solid membrane and diffuse into the liquor (Development of Biological Standard, Vol. 66, p. 263-268).

4) A method similar to the method 3), in which the pores of a porous hollow-fiber membrane are plugged with an oxygen-permeable solid material, and oxygen which has passed through the hollow-fiber membrane is diffused into and dissolved in a liquor (see Jap. Pat. Appln. Kokai (Laid-Open) No. 61-18402).

On the other hand, animal cells are roughly classified to anchorage-independent cells and anchorage-dependent cells according as their propagation requires or does not require a solid surface. For the propagation of the anchorage-independent cells, the method 1) of blowing oxygen directly through a liquor is suitable. For the propagation of the anchorage-dependent cells, a culturing method in which animal cells are attached to microbeads is often employed, and therefore a suitable oxygen-supplying method is the method 2) of blowing an oxygen-containing gas against the free surface of a culture liquor, or the method 3) or 4) which use an oxygen-permeable solid membrane or hollow-fiber membrane, respectively. The methods using the solid membrane or hollow-fiber membrane permit more efficient oxygen supply than does the method of blowing an oxygen-containing gas against the free surface of a culture liquor, but the amount of oxygen which can be supplied by the methods is limited, and when the methods are employed for highly productive high-density cell-culturing, the amount of oxygen supplied tends to be insufficient.

In particular, the method disclosed in Jap. Pat. Appln. Kokai (Laid-Open) No. 61-18402 does not always permit sufficient supply of oxygen because the material used for the plugging becomes a solid after molding.

In addition, fluorocarbons (organofluorine compounds) are known as solvents having a high affinity for oxygen. They have been noted as materials for artificial blood for a long time and have already been used in a certain type of artificial lung. There are known cases where the principle of the artificial lung is used as it is in an oxygen-supplying means for culturing animal cells (see Jap. Pat. Appln. Kokai (Laid-Open) Nos. 61-1383 and 64-60368).

In these cases, a volatile fluorocarbon and oxygen are brought into contact with each other outside a culture liquor tank, whereby oxygen is supported on the fluorocarbon. The fluorocarbon thus treated is added dropwise to a culture liquor in the culture liquor tank, and oxygen is diffused into the liquor during the precipitation of the fluorocarbon. Since the fluorocarbon having a high specific gravity precipitates finally in the bottom of the tank to undergo phase separation between it and the culture liquor, the fluorocarbon in the tank bottom is recovered by a suitable means, taken out of the tank, and then brought into contact with oxygen again to re-support oxygen.

However, in the method described above, the fluorocarbon which is expensive is used in a large amount and must be recycled continuously for a long period of time (1 to 2 months). Moreover, a considerable amount of the fluorocarbon is lost due to its volatility for this period. Therefore, the method does not meet the real demand for a low-cost, simple oxygen-supplying method.

SUMMARY OF THE INVENTION

The present invention is intended to provide an oxygen-dissolving process which solves such problems in the prior art, has a simple constitution entailing low cost and withstanding long-term operation, and has a high oxygen-supplying capability; and an apparatus for practicing this process. Furthermore, the present invention is intended to provide an oxygen-dissolving process for supplying oxygen dissolved in water to cells; a cell-culturing apparatus having a structure for supplying oxygen to cells by this process; and a culturing process using such an apparatus.

The present invention discloses and provides an oxygen-dissolving process in which for achieving the above object, an oxygen-permeable and water-insoluble liquid membrane is formed on a support layer made of a hydrophobic porous material, and one side of the liquid membrane is brought into contact with an oxygen-containing gas and the other side with an aqueous liquor, whereby oxygen is dissolved in the aqueous liquor; and an apparatus for practicing this process.

The liquid constituting the oxygen-permeable liquid membrane is a substantially water-insoluble liquid and is particularly preferably an organofluorine compound.

The present invention also discloses and provides a cell-culturing process comprising adding cells to an oxygen-containing aqueous liquor obtained by the above oxygen-dissolving process, and effecting cell-culturing in the liquor; and an apparatus for practicing this process.

In addition, the present invention discloses and provides an apparatus for culturing cells and the like which comprises a culture liquor tank; oxygen-dissolving means comprising a support layer made of a hydrophobic porous material and a liquid membrane formed thereon of an oxygen-permeable liquid; a means for supplying oxygen to one side of the oxygen-dissolving means; and a culture liquor phase in the culture liquor tank which is in contact with the other side of the oxygen-dissolving means.

In any of the above processes and apparatus of the present invention, the support layer made of a hydrophobic porous material may be either a sheet-like one or a hollow, tubular one.

Whether the support layer is a sheet-like one or a hollow, tubular one, the present invention provides a novel process for oxygen transfer and a novel apparatus therefor which have been developed by noting a oxygen-permeable liquid heretofore well-known as artificial blood and the like, and further improving its high oxygen-transferring capability, and which permit marked reduction of the amount of the expensive oxygen-permeable liquid used.

Figure 1:
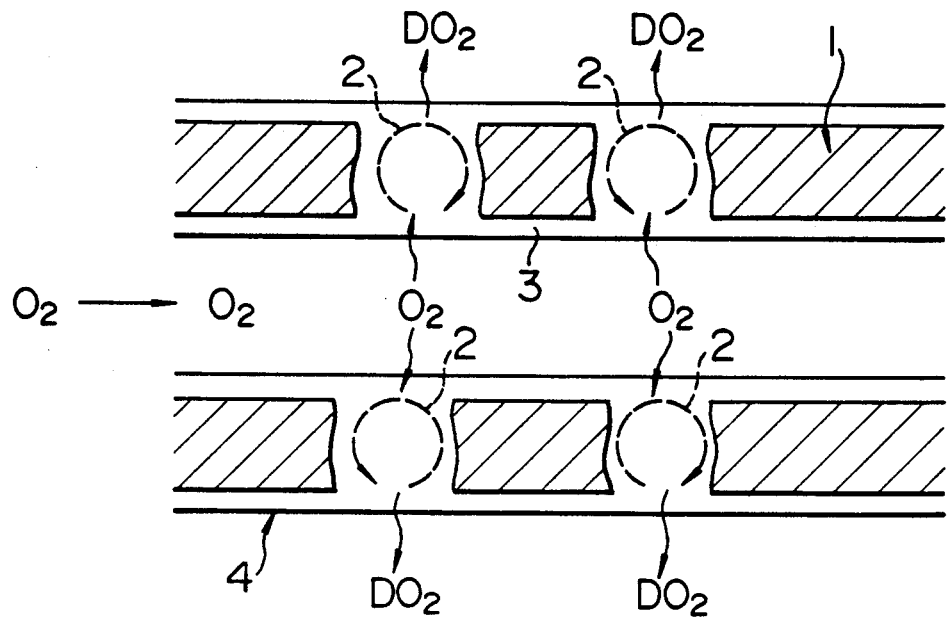
FIG. 1 is a schematic diagram for showing the outline of the oxygen-dissolving process of the present invention.

1 . . . hollow-fiber membrane,
2 . . . pore portion,
4 and 11 . . . perfluorocarbon-impregnated porous hydrophobic hollow-fiber membrane,
20 . . . culture liquor tank,
21 . . . culture medium,
22 . . . culture medium storage tank,
23 . . . culture supernatant,
24 . . . culture supernatant storage tank,
29 . . . cell-attached micro-beads,
71 . . . culture tank,
72 . . . liquid membrane (a perfluorocarbon-coated hollow-fiber membrane made of a porous polytetrafluoroethylene),
73 . . . agitating blade,
74 . . . jacket,
75 . . . dissolved oxygen controller and concurrently sequencer,
76 . . . aseptic filter,
77 . . . filtration tank for cell separation,
78 . . . hollow-fiber membrane for cell separation by filtration,
79 . . . solenoid valve,
80 . . . pump for culture medium supply,
81 . . . pump for culture supernatant withdrawal,
82 . . . oxygen gas cylinder,
83 . . . culture medium storage tank,
84 . . . culture medium,
85 . . . culture supernatant storage tank,
86 . . . culture supernatant,
87 . . . waste gas,
88 . . . motor for agitation.
89 . . . gas filter

DETAILED DESCRIPTION OF THE INVENTION

As the hydrophobic porous material, a material having a contact angle with water of 40° to 150° is used. When the contact angle is less than 40°, the oxygen-permeable liquid is liable to be released from a membrane of the hydrophobic porous material. For a practical material, the upper limit of the contact angle is 150°. There can be used heretofore well-known materials such as polypropylenes, polyethylenes, polysulfones, polyorganosilicons, polytetrafluoroethylenes, and derivatives thereof.

When the present invention is employed for supplying oxygen in pure culture of cells, suitable hydrophobic porous materials are those which are resistant to heating during steam sterilization, for example, polypropylenes, polysulfones, polyorganosilicons, and polytetrafluoroethylenes.

Although in principle, the diameter of pores of the hydrophobic porous material is such that the pores can be sufficiently plugged with the oxygen-permeable liquid, the diameter is preferably such that no air bubble is released from the surface of the hydrophobic porous membrane when the difference between the pressures on both sides of the membrane is 0.01 atm or more. A suitable range of the diameter is 0.05 to 300 $\mu$m. The form of the pores is not critical and the pores may have, for example, either a circular section or a slit-form section. A suitable range of the void ratio is 20 to 80%. When the void ratio is less than 20%, the permeation efficiency is low. When it exceeds 80%, the physical strength of the membrane is deteriorated.

As the oxygen-permeable liquid, a heretofore well-known material is used. The oxygen-permeable liquid is not critical so long as it is water-insoluble and substantially slightly volatile or nonvolatile. When the present invention is employed for culturing cells, the oxygen-permeable liquid is, of course, limited to those having no biological toxicity. Suitable examples of the oxygen-permeable liquid are linear or branched perfluoropolyethers having 10 to 200 carbon atoms, and linear, branched or cyclic perfluorocarbons having 8 or more carbon atoms which are liquid at 38° C. Of these, the perfluoropolyethers are particularly suitable for using for a long period of time without supply while preventing their volatilization substantially completely during steam sterilization and gas introduction.

The liquid membrane used in the present invention can easily be formed by coating or impregnating the hydrophobic porous membrane from the outside with the oxygen-permeable liquid. When the hydrophobic porous membrane is a hollow-fiber membrane, the liquid membrane can easily be formed by injecting the liquid into the tube, i.e., the hydrophobic porous membrane, to conduct coating or impregnation. The excess liquid adhering to the porous membrane can easily be removed by bringing the same into contact with an absorbent material such as paper.

When a single long hollow-fiber membrane is used as it is for a long period of time, a large pressure loss is caused. Therefore, aeration can be conducted more smoothly by using a module obtained by dividing the hollow-fiber membrane into pieces and binding a plurality of the pieces at both ends (see FIG. 4).

When supported on a hydrophobic porous membrane, the oxygen-permeable liquid forms a liquid membrane in which the hydrophobic porous membrane portion including pore portions is covered with the oxygen-permeable liquid and the pore portions are half fixed. Oxygen diffuses and transfers from the gas phase side of the liquid membrane, and oxygen on the reverse side, i.e., the aqueous liquor side, diffused into the aqueous liquor to be dissolved therein.

In this case, the liquid membrane permits continuous oxygen transfer, its thickness is much smaller than the particle size employed in a conventional liquid dropping method, and the oxygen-permeable liquid is held by the interfacial tension in the pores of the hydrophobic porous membrane. Therefore, the interface is always renewed by the flow of the liquid constituting the liquid membrane.

Accordingly, the liquid membrane, of course, enables more efficient oxygen transfer than does a conventional solid membrane. Moreover, the liquid membrane makes it possible to achieve oxygen transfer very efficiently by using the oxygen-permeable liquid in an amount much smaller than that employed in a conventional oxygen-permeable liquid dropping method.

DESCRIPTION OF THE PREFERRED EMBODIMENTS

Several examples of the present invention are described below in detail with reference to the attached drawings.

EXAMPLE 1

FIG. 1 is a schematic diagram showing one embodiment of the process for oxygen dissolution and apparatus therefor according to the present invention. That is, FIG. 1 is a cross-sectional view of a product 4 obtained by forming a liquid membrane 3 of a perfluorocarbon as one example of the oxygen-permeable liquid on a hydrophobic hollow-fiber membrane 1 made of a porous polytetrafluoroethylene as one example of the hydrophobic porous material. A large number of the pore portions 2 of the hydrophobic hollow-fiber membrane are, of course, filled with the perfluorocarbon.

An oxygen-containing gas is supplied to the hollow-fiber membrane 1 from one end of the membrane. By the contact of the oxygen-containing gas with the perfluorocarbon liquid membrane 3 formed on the whole inner surface of the hollow-fiber membrane 1, oxygen is incorporated into spaces among molecules in the liquid membrane. The oxygen incorporated transfers to the outer surface of the hollow-fiber membrane through the pores owing to the flow of the liquid constituting the liquid membrane or diffusion. Since the outer surface is in contact with a culture liquor phase, the oxygen incorporated diffuses into and dissolves in the culture liquor continuously.

In the present invention, as described above, the oxygen-permeable liquid is held by the interfacial tension in the pores of the hydrophobic porous membrane, and therefore the interface is always renewed by the flow of the liquid constituting the liquid membrane, in the inner and outer surface portions of the porous membrane and the pore portions. Accordingly, it becomes possible to attain a sufficient oxygen transfer rate for a long period of time by using the oxygen-permeable liquid in an amount much smaller than that employed in a conventional process or apparatus.

EXAMPLE 2

Figure 2:
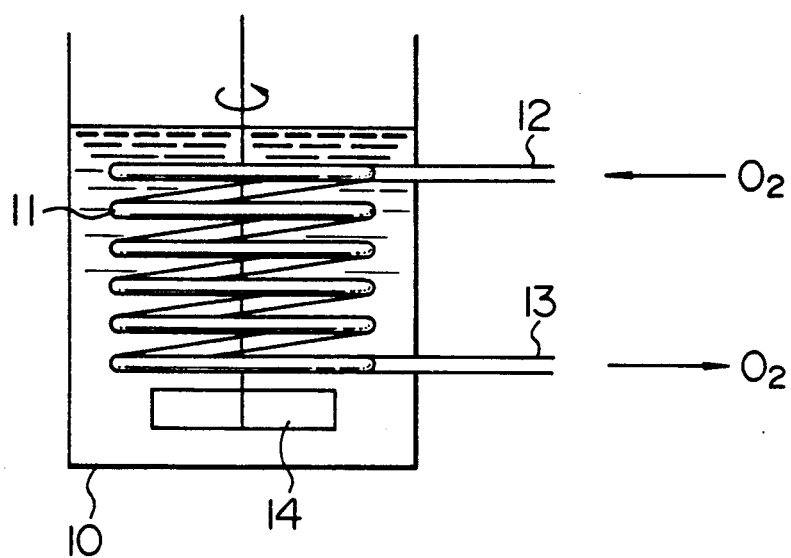
FIG. 2 is a cross-sectional view of an oxygen-dissolving apparatus for practicing the oxygen-dissolving process of the present invention.

In this example shown in FIG. 2, the oxygen-dissolving apparatus of the present invention schematically shown in Example 1 was used and the oxygen transfer rate was measured. About 5 m of a hollow-fiber membrane (pore diameter: 2 $\mu$m) made of a porous polytetrafluoroethylene having an inside diameter of 1 mm and an outside diameter of 2 mm was formed into a spiral shape, after which 5 ml of perfluorodecane was injected into the hollow-fiber membrane to be infiltrated into the membrane matrix including pores of the hollow-fiber membrane. The spiral hollow-fiber membrane 11 thus obtained was placed in a beaker 10 while extending the membrane so as to provide a gas inlet 12 and a gas outlet 13 outside the beaker. An impeller 14 rotatable by a proper means was placed in the beaker.

In the beaker 10 was placed 1 liter of pure water, and oxygen is introduced into the hollow-fiber membrane 11 through the gas inlet 12 at a rate of 0.1 liter/min under agitation conditions of 37° C. and 50 r.p.m. and discharged outside the fiber membrane through the gas outlet 13 at the other end. A dissolved oxygen (hereinafter referred to as "DO") electrode was placed in the water, and the oxygen transfer rate per unit area of the outer surface of the membrane was measured.

Consequently, the oxygen transfer rate of the membrane was 160 mmole $O_2/m^2 \cdot h$. The oxygen transfer rate per liter of water was 5 mmole $O_2/l \cdot h$.

COMPARATIVE EXAMPLE 1

The oxygen transfer rate was measured in the same manner as in Example 2, except that a hollow-fiber membrane made of a porous polytetrafluoroethylene which had not been treated with perfluorodecane was used in place of the hollow-fiber membrane of the present invention used in Example 2.

Consequently, the oxygen transfer rate was 30 mmole/$m^2 \cdot h$.

COMPARATIVE EXAMPLE 2

There was used the same apparatus as in Example 2, except for omitting the membrane of perfluorodecane used in Example 2, dropping oxygen-saturated perfluorodecane on the water surface at a rate of 100 ml/min through a single-hole nozzle having a circular hole with a diameter of 1 mm, and recycling the perfluorodecane precipitated in the bottom, by means of a pump. In this case, 200 ml of perfluorodecane was used.

Consequently, the oxygen transfer rate per liter of water was 2.2 mmole $O_2/l \cdot h$.

EXAMPLE 3

Figure 3:
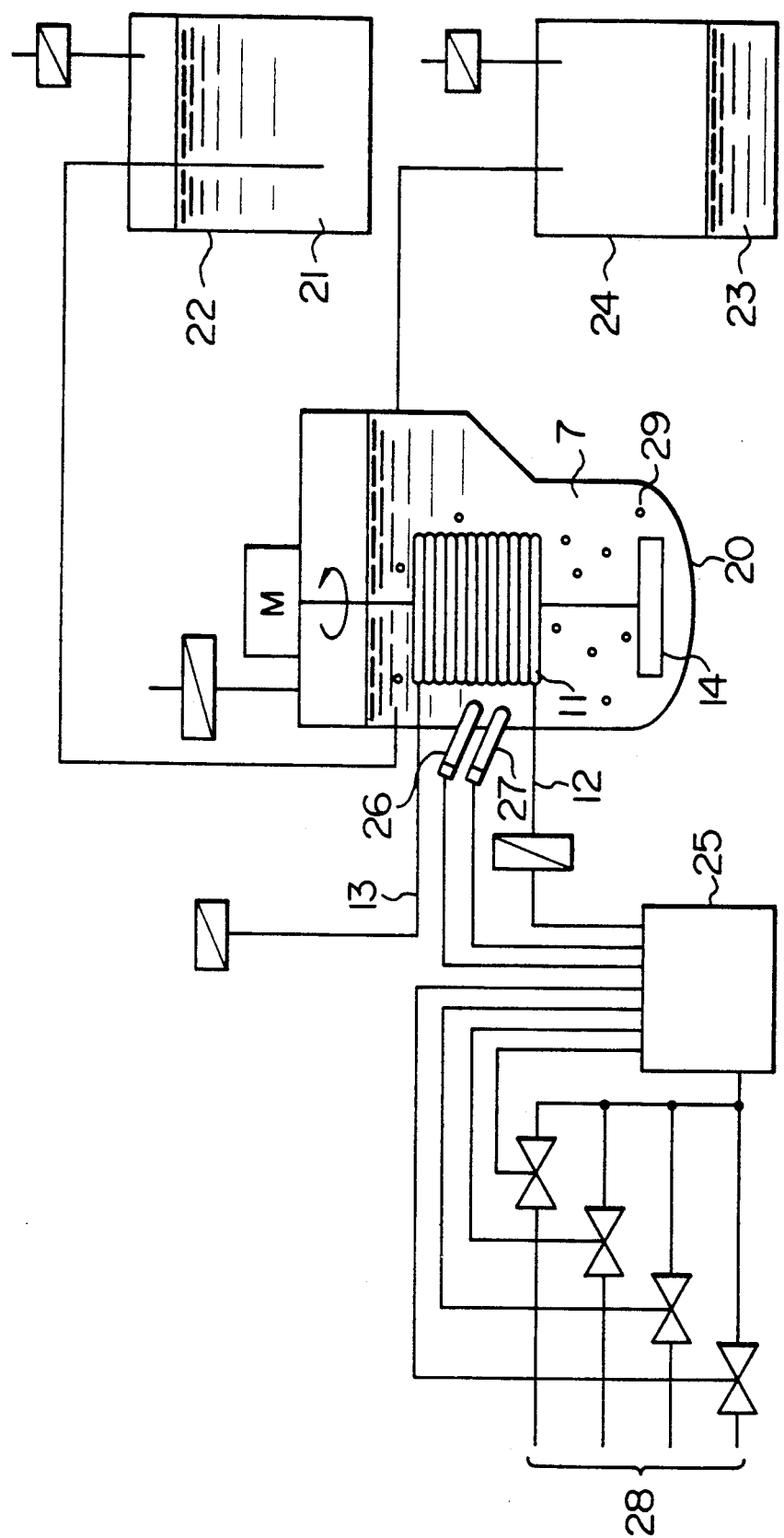
FIG. 3 is a schematic diagram of a culturing system for anchorage-dependent cells which uses the oxygen-dissolving process and apparatus of the present invention.

FIG. 3 shows a case where a polytetrafluoroethylene fiber membrane 11 treated with 10 ml of a perfluorodecane in the same manner as in Example 2 was used as a cell-culturing apparatus.

The culturing equipment used in this example is explained below. The hollow-fiber membrane 11 treated with the perfluorodecane is mounted in a culture liquor tank 20 so that a gas inlet 12 and a gas outlet 13 may have their respective openings in the wall of the tank 20. An impeller 14 is also mounted so as to be rotatable by means of a motor M. A culture medium storage tank 22 for storing a culture medium 21 and a culture supernatant storage tank 24 for storing a culture supernatant 23 are connected to the culture liquor tank 20 by suitable pipings, respectively.

In addition, a DO electrode 26 for measuring the oxygen concentration and a pH electrode 27 for measuring the pH are provided in the culture liquor tank 20 through a gas control panel 25 having a suitable control mechanism. The gas inlet 12 is also connected to the gas control panel 25, whereby a predetermined oxygen-containing gas is supplied. Gases such as air, oxygen, nitrogen and carbon dioxide gas are supplied to the gas control panel 25 through suitable pipings. In FIG. 3, numeral 29 shows micro-beads used for cell-culturing.

A cell-culturing test was carried out using the above equipment. Mouse spleen cells were cultured in the culture liquor tank (capacity: 5 liter) 20 by the micro-beads method. Eagle's MEM medium was supplemented with 10% bovine serum and maintained at 37° C., and cell-culturing was effected at a gas introduction rate to the hollow-fiber membrane of 0.2 liter/min and a concentration of cells inoculated of $1 \times 10^5$ cells/ml beads while rotating the impeller 14 at a rate of 50 r.p.m. The cell concentration after 5 days reached $1 \times 10^7$ cells/ml.

EXAMPLE 4

Figure 4:
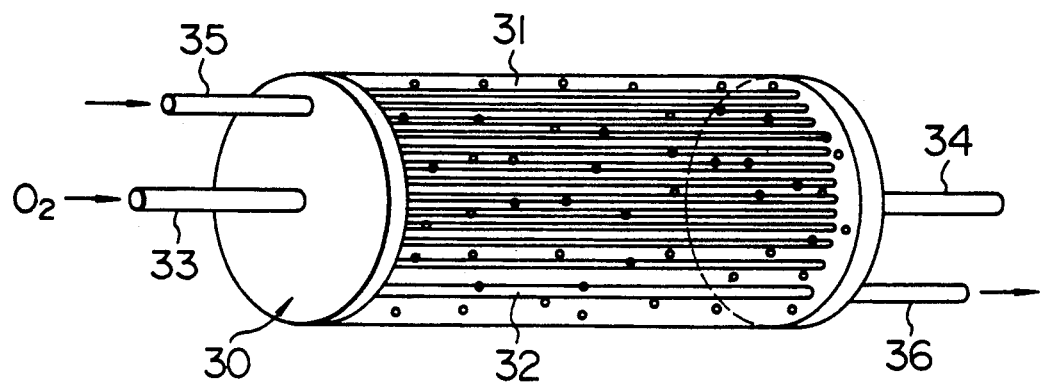
FIG. 4, FIG. 5, FIG. 6 and FIG. 7 are perspective views showing examples of culturing vessel and the like for anchorage-dependent cells to which the oxygen-dissolving process of the present invention is applied.

FIG. 4 shows further another cell-culturing apparatus of the present invention. In this hollow-fiber membrane cell-culturing apparatus 30, a plurality of hollow-fiber membranes 32 are provided inside a cylindrical casing 31 both end faces of which have been sealed. Each hollow-fiber membrane 32 communicates with an oxygen-containing gas inlet 33 provided at one sealed end of the casing 31. The other end of each hollow-fiber membrane 32 communicates with an oxygen-containing gas outlet 34 provided at the other sealed end of the casing 31, and a waste gas is discharged through the gas outlet 34.

In addition, an inlet 35 and an outlet 36 for a liquid medium are provided at the sealed ends, respectively, of the casing 31, and the medium is supplied or discharged through them, respectively.

The hollow-fiber membrane of the apparatus is a porous polysulfone hollow-fiber module impregnated with a perfluorocarbon. Oxygen supplied through the oxygen-containing gas inlet is incorporated among molecules of the perfluorocarbon and dissolves in a culture liquor in proportion to the movement of a liquid membrane.

Also in the apparatus used in the present example, cell-culturing was effected by filling the casing with micro-beads having cells attached thereto.

EXAMPLE 5

Figure 5:
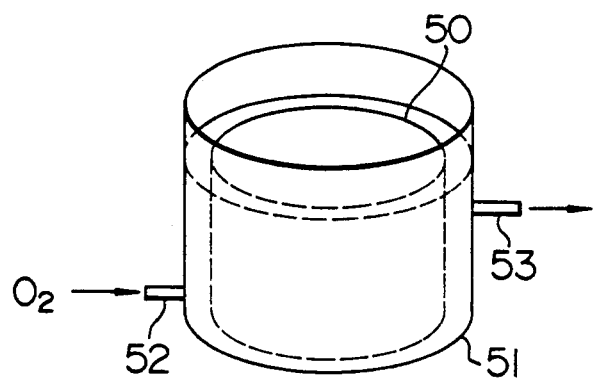

FIG. 5 shows still another example of the cell-culturing apparatus of the present invention. A hydrophobic porous support material is formed into a cylindrical member having a hollow inner part, and a fluorocarbon liquid membrane is formed on the cylindrical member in the same manner as in the above other examples. The cylindrical member 50 thus treated is placed in a culture liquor tank 51, and an oxygen-containing gas is supplied through an oxygen gas inlet 52. Numeral 53 shows a gas outlet.

EXAMPLE 6

Figure 6:
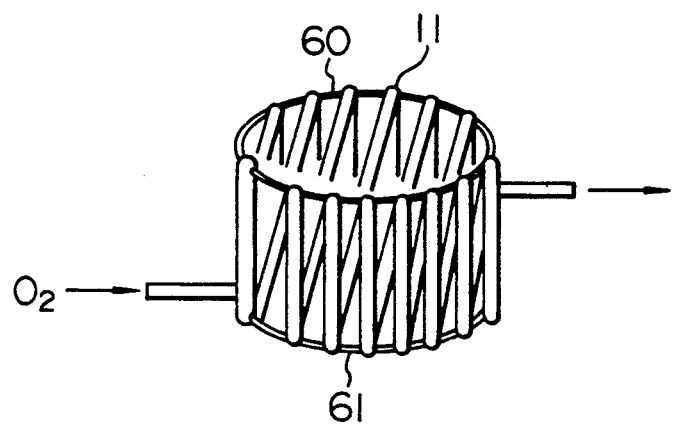

FIG. 6 shows further another mode of support on a hollow-fiber membrane. In this example, a hollow-fiber membrane 11 having an oxygen-permeable membrane formed thereon according to the present invention is wound round links 60 and 61 connected so as to held the link 60 over the link 61 at an appropriate distance.

The resulting assembly is placed in a suitable culture liquor tank and oxygen is supplied.

The embodiments described in Examples 5 and 6 are advantageous in that the internal space of the culture liquor tank can be effectively utilized.

EXAMPLE 7

Figure 7:
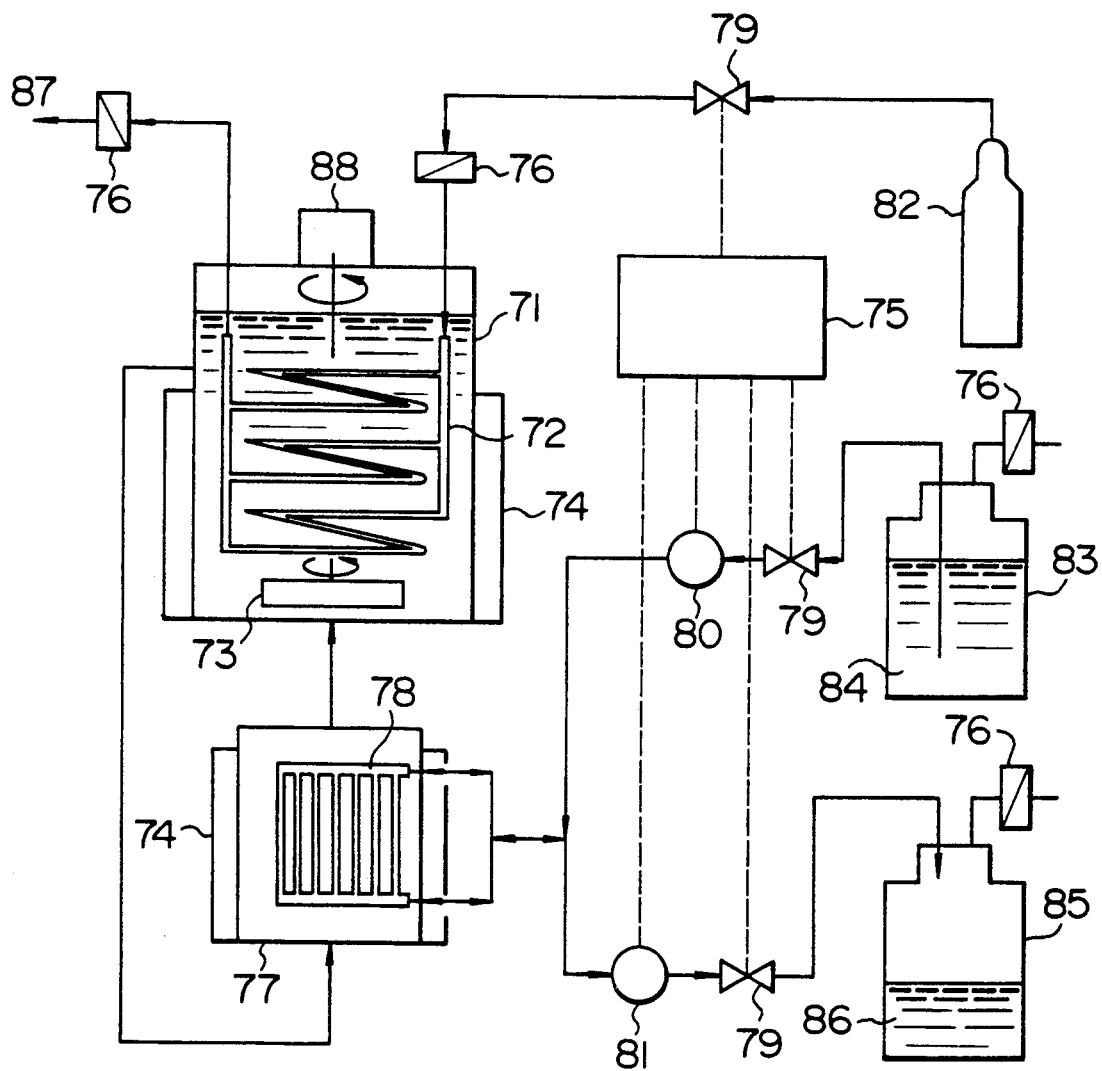

There is described below an example in which the equipment shown in FIG. 7 was used and a perfluoropolyether was used as a liquid membrane. In the apparatus, oxygen is diffused into a liquor by placing a liquid membrane 72 under the liquor in a tank, introducing oxygen gas into the liquid membrane 72 of hollow-fiber membrane form from a cylinder 82 through a solenoid valve 79 interlocked with a dissolved oxygen controller and concurrently sequencer 75, and agitating the liquor by means of a agitating blade 73. For realizing perfusion culture, a filtration tank for cell separation 77 with a capacity of 1 liter connected to the bottom of the culture tank is provided, and a hollow-fiber membrane for cell separation by filtration (made of a porous polytetrafluoroethylene and having an outside diameter of 2 mm, a pore diameter of 20 µm and a length of 10 m) is placed in the filtration tank 77. Cells are separated in the following manner. A culture supernatant is withdrawn by filtration under reduced pressure by means of a pump for culture supernatant withdrawal 81, after which a culture medium 84 is introduced into the hollow-fiber membrane 78 in the filtration tank 77 under pressure by means of a pump for culture medium supply 80, whereby back washing of the hollow-fiber membrane for cell separation by filtration 78 is conducted to disperse cells adhering to the membrane in the filtration tank 77. As the culture tank, there was used a cylindrical jaketted tank having a diameter of 15 cm and a height of 15 cm. As the support membrane of the liquid membrane, there was used a module obtained by parallel connection of three porous hollow-fiber membranes made of a polytetrafluoroethylene having an outside diameter of 4 mm, a length of 1 m, a porosity of 60% and a pore diameter of 2 to 20µ. The liquid membrane was formed by coating the outer surface of the support membrane with 4 ml of a perfluoropolyether having a chemical structure of $F—(C_nF_{2n}—O)_p—C_mF_{2m+1}$ (n=2 to 4, m=2 to 4; average molecular weight $1 \times 10^4$). The equipment was sterilized by steam and a culture medium was charged into the culture tank and the filtration tank in a total amount of 2.5 liters. To the culture medium in the culture tank was added 0.5 liter of a culture broth of rat cancerous cells of JTC-1 strain cultured in a roller bottle by the use of a Dulbecco's Modified Eagle's medium supplemented with 10 vol % bovine serum, whereby the cells were inoculated to adjust the cell concentration to $4 \times 10^5$ cells/ml The dissolved oxygen concentration in the culture tank was controlled by introducing oxygen gas into the hollow fibers of the liquid membrane at a rate of 10 ml/min and opening and closing the solenoid valve automatically so as to adjust the DO concentration to a preset concentration of 1.5 ppm. On the other hand, perfusion was carried out at a medium replacement rate of 3 liters/day by repeating the following procedure three times a day: one-third of the culture liquor in the culture tank was filtered, followed by back washing of a filter membrane with the culture medium in the same volume as that of the culture liquor filtered. Agitation in the culture tank was conducted at a constant rate of 60 r.p.m. The results obtained are shown in Table 1. The results indicate that the liquid membrane according to the present invention has such an oxygen supplying capability as enables the adjustment of the DO concentration to 1.4 to 1.6 all during the cell-culturing, and that the liquid membrane permits cell-culturing with a high cell density of more than $1 \times 10^7$ cells/ml.

TABLE 1

| Item | Number of culturing days elapsed (days) | | | | | |
|---|---|---|---|---|---|---|
| | 0 | 1 | 2 | 5 | 10 | 15 | 20 |
| DO concentration (ppm) | | | | 1.4–1.6 | | | |
| Viable cell concentration ($\times 10^6$ cells/ml) | 0.40 | 0.60 | 1.0 | 2.5 | 6.0 | 10 | 11 |

EXAMPLE 8

Rat cancerous cells of JIC-1 strain were cultured in the same manner as in Example 7 by the use of the same equipment as in Example 7, except for using 4.5 ml of a polyfluoroether with an average molecular weight of 8,000 represented by the formula

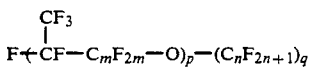

(wherein q is 1 to 5) as a material for a liquid membrane, and changing the concentration of cells inoculated to $0.52 \times 10^6$ cells/ml. The results obtained are shown in Table 2. The results indicate that as in Example 7, the liquid membrane used in Example 8 has such an oxygen-supplying capability as enables the adjustment of the DO concentration to 1.4 to 1.6 all during the cell-culturing, and that the liquid membrane permits cell-culturing with a high cell density of more than $1 \times 10^7$ cells/ml.

TABLE 2

| Item | Number of culturing days elapsed (days) | | | | | |
|---|---|---|---|---|---|---|
| | 0 | 1 | 2 | 5 | 10 | 15 | 20 |
| DO concentration (ppm) | | | | 1.4–1.6 | | | |
| Viable cell concentration ($\times 10^6$ cells/ml) | 0.52 | 0.73 | 1.2 | 3.3 | 9.0 | 12.0 | 12.5 |

COMPARATIVE EXAMPLE 3

Rat cancerous cells of JIC-1 strain were cultured in the same manner as in Examples 7 and 8, except that in place of the liquid membranes used in Examples 7 and 8, there was used as oxygen-permeable membrane a membrane obtained by using as support membrane the same polytetrafluoroethylene membrane as used in Examples 7 and 8, and plugging the pores of the polytetrafluoroethylene membrane with solid silicone rubber. The membrane used as oxygen-permeable membrane was prepared by applying 4.6 ml of uncured silicone rubber paste on the surface of the support membrane, and curing the same by maintaining the thus treated support membrane at 37° C. for 2 days. The concentration of cells inoculated was $0.40 \times 10^6$ cells/ml. The results of the culturing are shown in Table 3. The plugging of the pores of the support membrane with the solid could not meet the demand for oxygen the consumption of which increases with an increase the cell concentration during the culturing, and the DO concentration decreased at the fifth day. Therefore, the cell concentration reached only about one-fifth of that attained in Example 7.

TABLE 3

| Item | Number of culturing days elapsed (days) | | | | |
|---|---|---|---|---|---|
| | 0 | 1 | 2 | 5 | 10 | 15 |
| DO concentration (ppm) | | 1.4–1.6 | | | 0.1–0.2 | 0.01 |
| Viable cell concentration ($\times 10^6$ cells/ml) | 0.40 | 0.61 | 1.1 | 2.5 | 2.6 | 2.4 |

As is clear from the results described above, the present invention makes it possible to diffuse and dissolve oxygen in an aqueous liquor at a higher speed, as compared with conventional oxygen-suppling methods or cell-culturing apparatus using the methods. Furthermore, according to the present invention, the amount of an expensive perfluorocarbon used can be reduced to at most one-tenth of that employed in a conventional perfluorocarbon dropping method, and therefore the operation cost can be greatly reduced.

What is claimed is:

1. A process for dissolving oxygen comprising forming a liquid membrane of an oxygen-permeable water-insoluble liquid on a support layer made of a hydrophobic porous material, bringing one side of the liquid membrane into contact with an oxygen-containing gas and the other side with an aqueous liquor, and thereby dissolving oxygen in the aqueous liquor.

2. A process for dissolving oxygen according to claim 1, wherein the oxygen-permeable liquid is an organofluorine compound.

3. A process for dissolving oxygen according to claim 2, wherein the organofluorine compound is slightly volatile.

4. A process for dissolving oxygen according to claim 3, wherein the organofluorine compound is perfluoropolyether.

5. A process for dissolving oxygen according to claim 1, wherein the aqueous liquor is a culture liquor of cells.

6. A process for dissolving oxygen according to claim 5, wherein the oxygen-permeable water-insoluble liquid has no biological toxicity.

7. A process for culturing cells comprising adding cells to an oxygen-containing aqueous liquor obtained by the process according to claim 1, and conducting cell-culturing.

8. A process for culturing cells according to claim 7, wherein the oxygen-permeable water insoluble liquid has no biological toxicity.

9. A process for dissolving oxygen according to claim 1, wherein the hydrophobic porous material is selected from the group consisting of polypropylene, polyethylene, polysulfone, polyorganosilicon and polytetrafluoroethylene; said material having pores with diameters ranging from 0.05 to 300 μm, a void ratio of from 20 to 80% and hydrophobic surfaces contacting said oxygen-permeable water-insoluble liquid.

10. A process for dissolving oxygen according to claim 9, wherein the oxygen-permeable water-insoluble liquid is a linear or branched perfluoropolyether having 10 to 20 carbon atoms or a linear, branched or cyclic perfluorocarbon having at least 8 carbon atoms which is liquid at 38° C.

11. A process for dissolving oxygen according to claim 1, wherein the oxygen-permeable water-insoluble liquid has no biological toxicity.

* * * * *